(12) United States Patent
Törnsten et al.

(10) Patent No.: US 11,707,575 B2
(45) Date of Patent: Jul. 25, 2023

(54) EXCHANGEABLE CARTRIDGE FOR AN INJECTION DEVICE

(71) Applicant: Q-MED AB, Uppsala (SE)

(72) Inventors: Jonas Törnsten, Uppsala (SE); Max Blomqvist, Uppsala (SE); Joël Fontannaz, Bulle (CH); Elise Gortchacow, Wabern (CH)

(73) Assignee: Galderma Holding SA, Zug (CH)

(*) Notice: Subject to any disclaimer, the term of this patent is extended or adjusted under 35 U.S.C. 154(b) by 490 days.

(21) Appl. No.: 16/906,744

(22) Filed: Jun. 19, 2020

(65) Prior Publication Data
US 2020/0316304 A1  Oct. 8, 2020

Related U.S. Application Data

(63) Continuation of application No. PCT/EP2018/085718, filed on Dec. 19, 2018.

(30) Foreign Application Priority Data

Dec. 21, 2017 (EP) ..................................... 17209659

(51) Int. Cl.
*A61M 5/315* (2006.01)
*A61M 5/31* (2006.01)
*A61M 5/32* (2006.01)

(52) U.S. Cl.
CPC ...... *A61M 5/31505* (2013.01); *A61M 5/3129* (2013.01); *A61M 5/3202* (2013.01);
(Continued)

(58) Field of Classification Search
CPC .............. A61M 5/315; A61M 5/31511; A61M 5/31501; A61M 5/31505; A61M 5/31515;
(Continued)

(56) References Cited

U.S. PATENT DOCUMENTS 4,869,720 A  9/1989 Chernack
2008/0171999 A1  7/2008 Baplue et al.
(Continued)

FOREIGN PATENT DOCUMENTS

GB  0 781 554 A  8/1957
WO  WO-00/32259 A2  6/2000
WO  WO-2015/090731 A1  6/2015

OTHER PUBLICATIONS

International Search Report dated Mar. 6, 2019 received in corresponding International Application No. PCT/EP2018/085718 (4 pages).

*Primary Examiner* — Nathan R Price
*Assistant Examiner* — Anna E Goldberg-Richmeier
(74) *Attorney, Agent, or Firm* — Sunit Talapatra; Foley & Lardner LLP

(57) ABSTRACT

An exchangeable cartridge for an injection device is disclosed. The cartridge (3) comprises a container (4) and a plunger (10) connectable with a plunger rod (9). The container receives the plunger rod from its rear end. The plunger comprises a rod connector (12) connectable with a front portion (13), and the rod connector has a base portion (24), an outer wall section (15), an inner wall section (16), and a rod stop portion (17) encircled by the inner wall section. The inner wall section comprises several tongues (22) protruding rearwards from the base portion and defining an entrance opening (18) for the plunger rod. The inner wall section receives a front portion (13) of the plunger rod through the entrance, and the tongues are provided with retaining portions arranged to retain the front end portion during retraction of the plunger rod within the housing.

14 Claims, 9 Drawing Sheets

(52) U.S. Cl.
CPC ..... *A61M 5/31511* (2013.01); *A61M 5/31515* (2013.01); *A61M 2005/3142* (2013.01); *A61M 2205/273* (2013.01)

(58) Field of Classification Search
CPC .. A61M 5/14566; A61M 5/24; A61M 5/5066; A61M 2005/2403; A61M 2005/2411; A61M 2005/3142; A61M 2205/273
See application file for complete search history.

(56) References Cited

U.S. PATENT DOCUMENTS

2009/0299288 A1\* 12/2009 Sie .................... A61M 5/31515
604/151
2016/0310674 A1\* 10/2016 Törnsten ................ A61M 5/24

\* cited by examiner

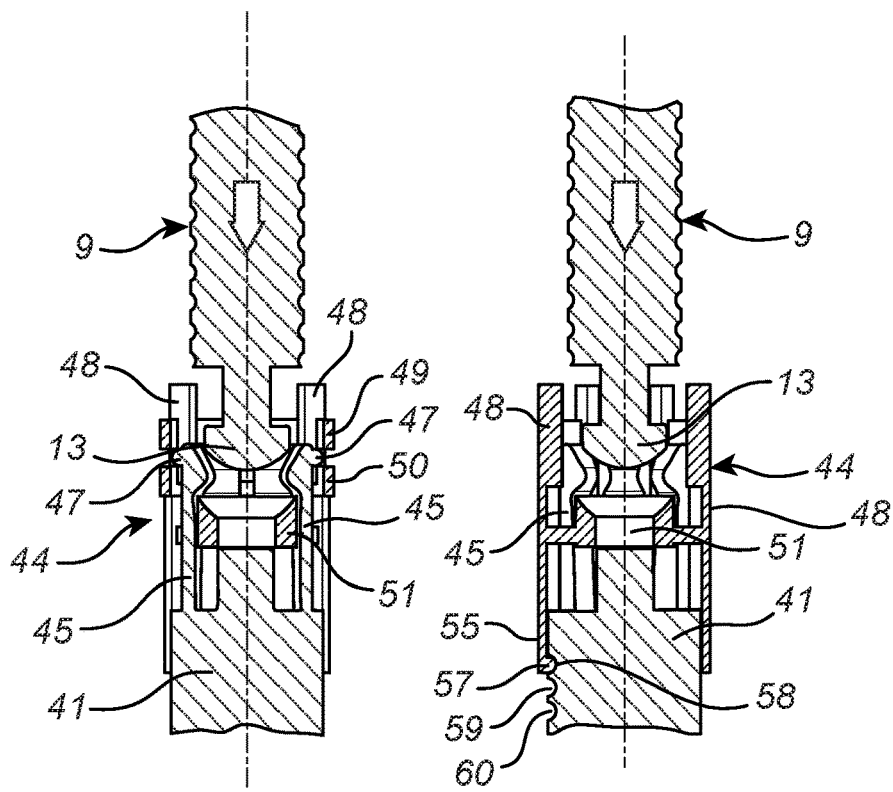
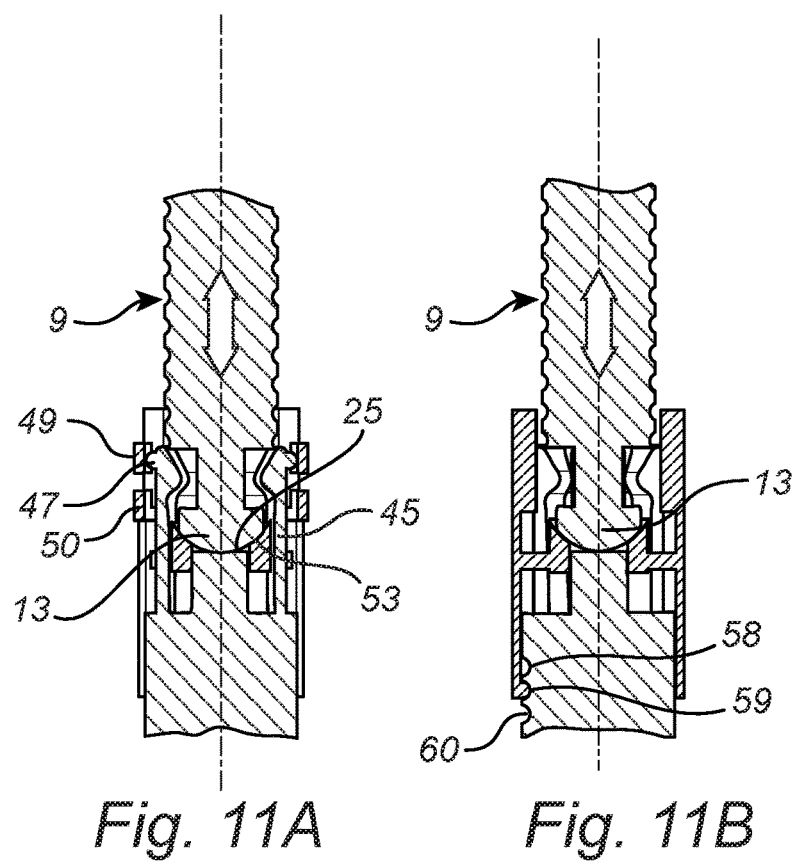

EXCHANGEABLE CARTRIDGE FOR AN INJECTION DEVICE

CROSS-REFERENCE TO RELATED APPLICATIONS

This application is a continuation of International Application No. PCT/EP2018/085718 filed Dec. 19, 2018, which claims the benefit of and priority to European Application No. 17209659.6 filed Dec. 21, 2017, both of which are hereby incorporated by reference herein in their entireties.

FIELD OF THE INVENTION

The present invention relates to an exchangeable cartridge containing a liquid composition, for an injection device for delivering the liquid composition, and to an injection device comprising such an exchangeable cartridge.

BACKGROUND OF THE INVENTION

A known injection device and a known exchangeable cartridge are disclosed in WO 2015/090731, where the cartridge comprises a plunger rod connector (7) having wall sections (10) extending rearwards, towards a plunger rod entrance of the cartridge. The wall sections define an entrance opening of the connector at a rear end thereof. At the rear end, each wall section has a heel portion extending radially inwards from an inner surface of the wall section, and a small resilient portion at an outer surface thereof. Each wall section has a front and a rear wall section, which are interconnected. When the plunger rod is introduced into the connector, the rear wall sections are forced to bend outwards during passage of a front portion of the plunger rod passed the heels, wherein the resilient portions are activated and pushes the wall sections back after the passage. This construction works well, but the wall sections are relatively complicated to manufacture.

SUMMARY OF THE INVENTION

It would be advantageous to provide a solution for a cartridge which is simpler to produce.

To better address this concern, in a first aspect of the invention there is presented an exchangeable cartridge containing a liquid composition, for an injection device for delivering the liquid composition, wherein the cartridge comprises a housing having a front end and a rear end, and a plunger slidably arranged within the housing. The plunger is connectable with a plunger rod of the injection device, wherein the housing is arranged to receive the plunger rod from its rear end. The plunger comprises a rod connector connectable with a front end portion of the plunger rod, wherein the rod connector has a base portion, an outer wall section extending rearwards from the base portion, an inner wall section extending rearwards from the base portion, and a rod stop portion encircled by the inner wall section. The inner wall section comprises several tongues protruding rearwards from the base portion, and defining an entrance opening for the plunger rod, wherein the inner wall section is arranged to receive a front portion of the plunger rod through the entrance opening. The tongues are provided with retaining portions, which are arranged to retain the front portion during retraction of the plunger rod within the housing. With the structure of the outer wall section and the inner wall section, which connects with the front portion of the plunger rod, a less complex structure, keeping interesting advantages of the cartridge of WO 2015/090731 has been enabled.

In accordance with an embodiment of the exchangeable cartridge, the housing is provided with a disposable cap, which covers at least a part of an opening of the housing at the rear end of the housing, and which constitutes a rear stop for the rod connector. This embodiment advantageously involves the cap in the solution for providing the plunger rod connection/disconnection function.

In accordance with an embodiment of the exchangeable cartridge, the outer wall section of the rod connector is arranged to abut on the disposable cap in a rearmost position. It is advantageous to use the outer wall for this purpose, since then the inner wall section can be made less complicated.

In accordance with an embodiment of the exchangeable cartridge, the width of the entrance opening is smaller than a maximum width of the front end portion, and it has at least the same width as the width of a rod portion adjacent to and rear of the front end portion. The tongues are resilient for enabling the front end portion to pass the entrance opening upon exerting an opening force on the tongues. According to this embodiment a reliable interconnection is obtained in a simple way.

In accordance with an embodiment of the exchangeable cartridge, each retaining portion comprises a shoulder arranged at a rear end of the tongue at an inner side thereof, the shoulder protruding radially inwards.

In accordance with an embodiment of the exchangeable cartridge, the rod stop portion comprises a centre pin protruding rearwards from the base portion.

In accordance with an embodiment of the exchangeable cartridge, the entrance opening and the rod stop portion are arranged at a distance to each other which enables a longitudinal play between the front end portion of the plunger rod on one hand and the entrance opening and the rod stop portion on the other hand, when the rod connector is connected to the front end portion. Thereby the front end portion is enabled to move back and forth between the entrance opening and the rod stop portion without moving the plunger.

In accordance with an embodiment of the exchangeable cartridge, the outer wall section comprises several longitudinally elongated post elements, positioned in the gaps between the tongues.

In accordance with an embodiment of the exchangeable cartridge, the outer wall section comprises a rear ring, and a front ring, which is longitudinally parallel to the rear ring, wherein the rear and front rings are integral with the post elements, wherein the rear and front rings extend outside of the tongues, and wherein there is a gap between the rear and front rings.

In accordance with an embodiment of the exchangeable cartridge, end portions of some of the post elements are provided with a respective inner protrusion, wherein the base portion, at each post element having such an inner protrusion, is provided with several consecutive recesses, which are arranged to be able to receive the inner protrusion of the post element.

In accordance with an embodiment of the exchangeable cartridge, the outer wall section further comprises a rod seat at the centre thereof, which rod seat has a tubular portion, which is positioned concentrically of the rod stop portion, and a ring shaped collar portion encircling the periphery of the tubular portion at its rear end, wherein the collar portion has a curved surface, which mates with a bulging front surface of the front end portion, and wherein the post elements are integral with the rod seat, and are connected with the rod seat via a respective spoke element.

In accordance with an embodiment of the exchangeable cartridge, the outer wall section is a tubular portion.

According to another aspect of the present invention, there is provided an injection device for delivering a liquid composition, which comprises a generally elongated housing, holding an exchangeable cartridge as described above.

BRIEF DESCRIPTION OF THE DRAWINGS

The invention will now be described in more detail and with reference to the appended drawings in which:

FIG. 10A is a cross-sectional view of the part of the second embodiment;

FIG. 10B is another cross-sectional view of the part of the second embodiment;

FIG. 11A is yet another cross-sectional view of the part of the second embodiment;

FIG. 11B is still yet another cross-sectional view of the part of the second embodiment;

DESCRIPTION OF EMBODIMENTS

Figure 1:
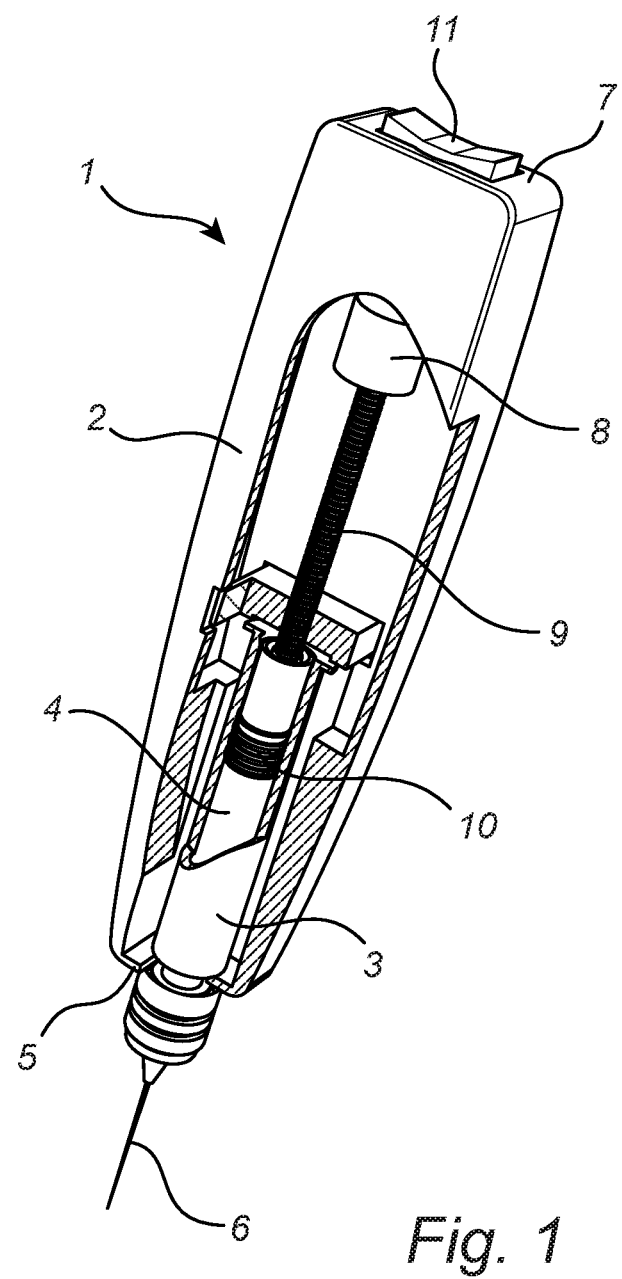
FIG. 1 is a perspective and partly cutaway view showing an embodiment of an injection device according to the present invention.
Figure 2A:
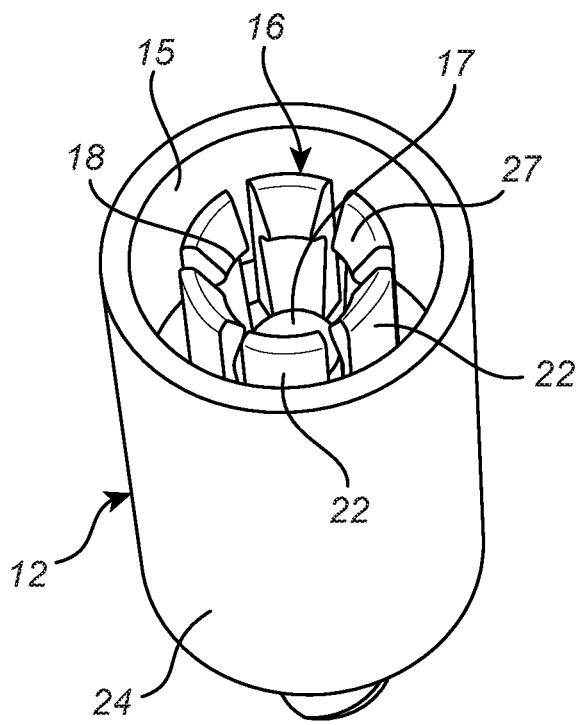
FIG. 2a is a perspective view of a part of the injection device of FIG. 1.
Figure 2B:
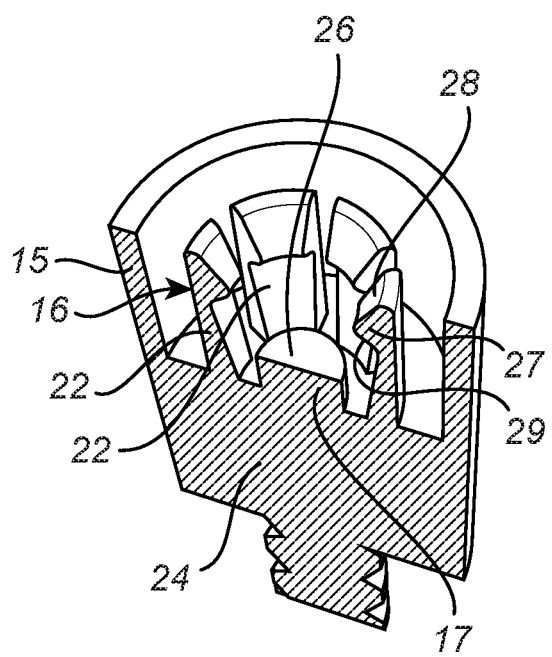
FIG. 2b is a partly perspective view of a part of the injection device of FIG. 1.

An overall view of a first embodiment of the injection device is shown in FIG. 1. The injection device 1 comprises a generally elongated housing 2, arranged to hold an exchangeable cartridge 3 comprising a container 4 containing a liquid composition to be injected. In FIG. 1 the injection device 1 is shown with the cartridge 3 held at the housing 2, here more particularly mounted therein. The injection device 1 has a front end 5, where an injection needle 6 of the cartridge 3 is located, and a rear end 7 opposite of the front end 5. The housing 2 comprises a drive device 8, and a plunger rod 9, which is connected with the drive device 8, and which is connectable to a plunger 10 within the cartridge 3, and more particularly within the container 4, for driving the plunger 10 within the cartridge.

Figure 3:
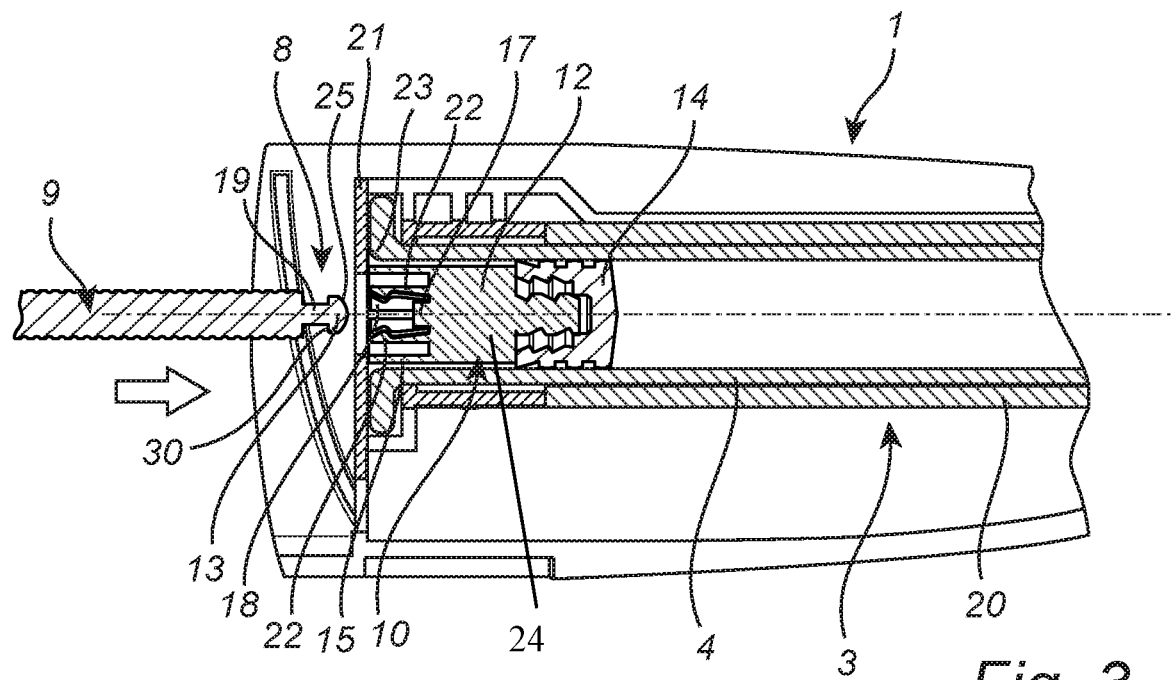
FIG. 3 is a partly sectional views showing a part of the injection device of FIG. 1 in different operational stages.

An operation button 11 for respective forward and rearward operation of the plunger rod 9, is arranged at the rear end 7. This is just an illustrative example. The button can be arranged at other positions of the housing 2, and there can be more than one button, etc. The outer shape of the injection device 1 can be largely varied, etc. More particularly, in this embodiment, the plunger rod 9 is rotatably attached to the drive device 8 for rotation about a longitudinal axis of the plunger rod 9, and is arranged to be rotated in order to be longitudinally moved. As shown in FIG. 3, the exchangeable cartridge 3 further comprises a sleeve 20 enclosing the container 4 and being configured for an accurate and engaging mounting of the cartridge 3 at the housing 2. It should be noted, though, that embodiments without the sleeve 20 are possible as well. At a front end of the container 4 it is connected with the needle 6 for ejecting the liquid through the needle 6, and at an opposite rear end of the container 4 it is provided with a disposable cap 21. In this embodiment, the disposable cap 21 is a plate shaped element covering a rear mouth 23 of the container 4. Furthermore, in this embodiment the disposable cap 21 is an integral portion of the exchangeable cartridge 3, and more particularly of the sleeve 20. However, other embodiments with a disposable cap being a separate detail or a portion of the container 4 are feasible within the scope of this invention.

Referring to FIGS. 1-7, the plunger 10 comprises a rod connector 12 for connecting with a front end portion 13 of the plunger rod 9, and a front plunger portion 14, which is connected with the rod connector 12, and which is configured to seal the container 4 and to contact the liquid therein. For instance, the rod connector 12 and the front plunger portion 14 are separately manufactured and fitted together with a screw joint at an appropriate occasion. The rod connector 12 has an outer wall section 15, and an inner wall section 16, which is concentric with the outer wall section 15, and a rod stop portion 17, encircled by the inner wall section 16. The inner wall section 16 defines an entrance opening 18. The width of the entrance opening 18 is smaller than the width of the front end portion 13, and the width of an intermediate rod portion 19 adjacent to and rear of the front end portion 13 is at most the same as, and preferably smaller than, the width of the entrance opening 18. More particularly, the inner wall section 16 comprises tongues 22 arranged side by side in a circle. The tongues 22, and thus the inner wall section 16, are resilient for enabling the front end portion 13 to pass the entrance opening 18 upon exerting a large enough force on the tongues 22. The rod stop portion 17 defines a central pin, i.e. a pin shaped protrusion.

There is a longitudinal play between the front end portion 13 of the plunger rod 9 on one hand and the entrance opening 18 and the rod stop portion 17 on the other hand. In other words, the distance between the entrance opening 18 and the rod stop portion 17 exceeds the length of the front end portion 13 Thereby it is possible for the front end portion 13 to move back and forth between the entrance opening 18 and the rod stop portion 17 without moving the plunger 10.

More particularly, the rod connector 12 can be regarded as comprising a base portion 24, as a main part of the rod connector, which base portion 24 is cylindrical in this embodiment, wherein the rod stop portion 17, i.e. the central pin 17, the inner wall section 16, i.e. the tongues 22, and the outer wall section 15, which is a tubular portion, are integral with the base portion 24, and extend concentrically rearwards thereof.

The front end portion 13 of the plunger rod 9 is provided with a bulging front surface 25 at the front end of the plunger rod 9, which is arranged to abut on an abutment surface 26 at the rear end of the rod stop portion 17 in an injection position, as will be further explained below. The bulging shape facilitates passage of the entrance opening 18.

The rod connector 12 has been assembled with the front plunger portion 14 and the assembled plunger 10 has been inserted into the container 4 comprised in the cartridge 3 such that the outer wall section 15 abuts on an inner surface of the liquid container 4. As an alternative assembling process, the front plunger portion 14 alone is mounted in the container 4, in conjunction with filling the container 4, and the rod connector 12 is mounted at a later stage.

As least some of the tongues 22 of the inner wall section 16, and preferably all tongues 22, each has a retaining portion 27, which in this embodiment is formed as an inner protrusion, or heel, which protrudes inwards, i.e. towards the centre of the rod connector 12, and which has an inclined entrance surface 28, which is inwardly inclined in a direction towards the front end of the rod connector 12. Each retaining portion 27 has a further surface 29 facing forwards and thus being at acute angle to the entrance surface 28. Thereby, the retaining portions 27 define the entrance opening 18.

Figure 4:
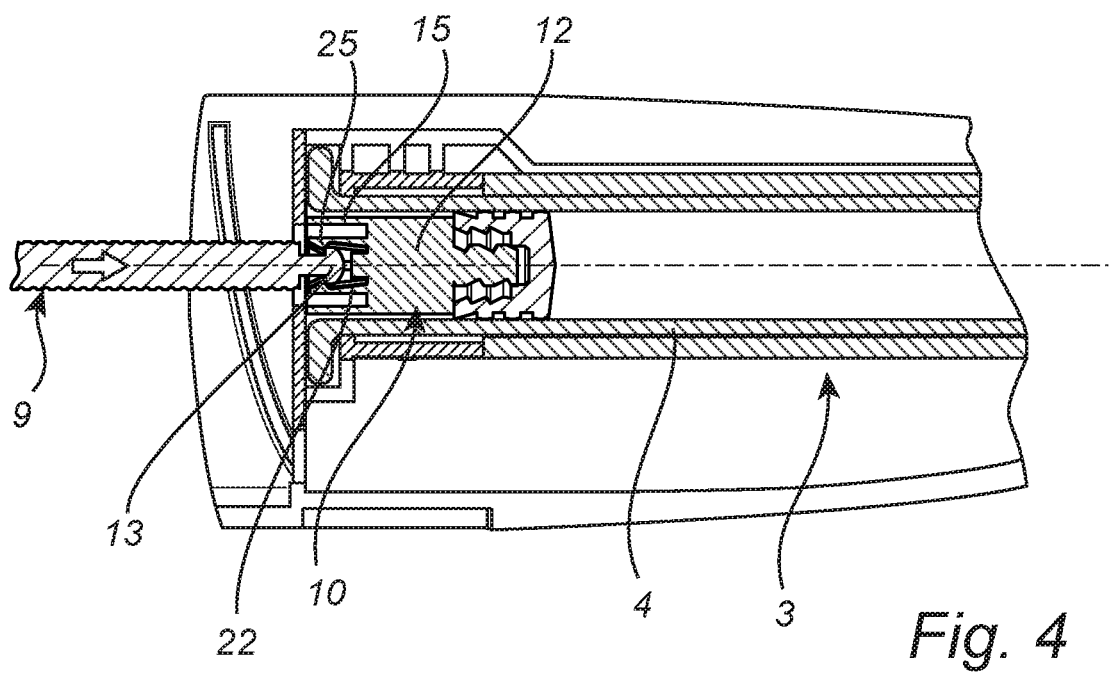
FIG. 4 is another partly sectional views showing a part of the injection device of FIG. 1 in different operational stages.
Figure 5:
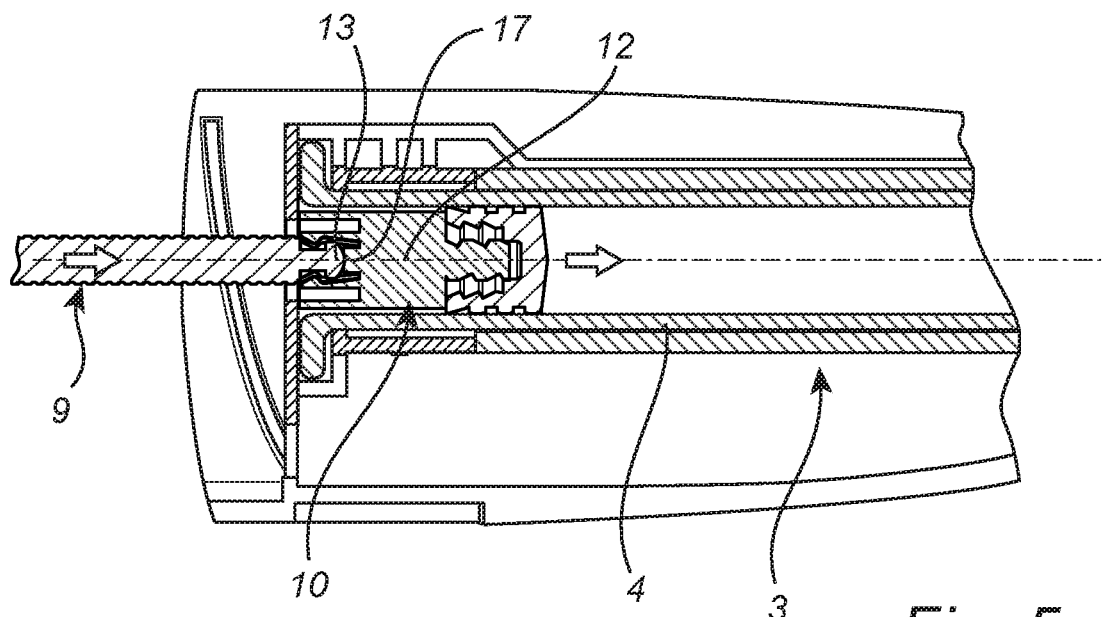
FIG. 5 is yet another partly sectional views showing a part of the injection device of FIG. 1 in different operational stages.

Referring to FIGS. 3-7, the injection device 1 is operated as follows. After having inserted a cartridge 3 into the housing 2, the plunger 10 is in its rearmost position, and the plunger rod 9 is positioned at the rear of the disposable cap 21, as shown in FIG. 3. Then the drive device 8 is activated by means of the operation button 16 for forwards operation, the plunger rod 9 is driven forward, and the front end portion 13 of the plunger rod 9 is entered into the rod connector 12 passed the entrance opening 18 by widening it, i.e. by engaging with the entrance surfaces 28 of the tongues 22, and sliding along the entrance surfaces 28 while bending the tongues 22 outwards, i.e. towards the outer wall section 15, as shown in FIG. 4. When the front end portion 13 has fully passed the retaining portion 27 at the entrance opening 18, the tongues 22 return to their idle position and the entrance opening 18 is closed to its original width. The front end portion 13 is now located within the space between the entrance opening 18, as defined by retaining portions 27, and the abutment surface 26 of the rod stop portion 17. It takes a certain fore to enter the front end portion into the rod connector 7. For a situation where the needle 6 is mounted after the interconnection of the plunger rod 9 and plunger 10, and more particularly the front end portion 8 and the rod connector 7, the plunger 6 is not movable, due to the incompressible liquid of the container 4. However, if the needle 6 is mounted before driving the plunger rod 9 into connection with the plunger 10, then the entrance force needed will have to be smaller than the resistance caused by the viscosity of the liquid and the friction against the wall of the container 4. Alternatively, some kind of additional mechanical hindrance can be provided, such as the circumferential rib (356) shown in WO0032259. At further forward movement of the plunger rod 9, its front surface 25 abuts on the abutment surface 26 of the rod stop portion 17, and the plunger rod 9 starts pushing the plunger 10 forward, thereby ejecting the liquid through the needle 6, as shown in FIG. 5.

Figure 6:
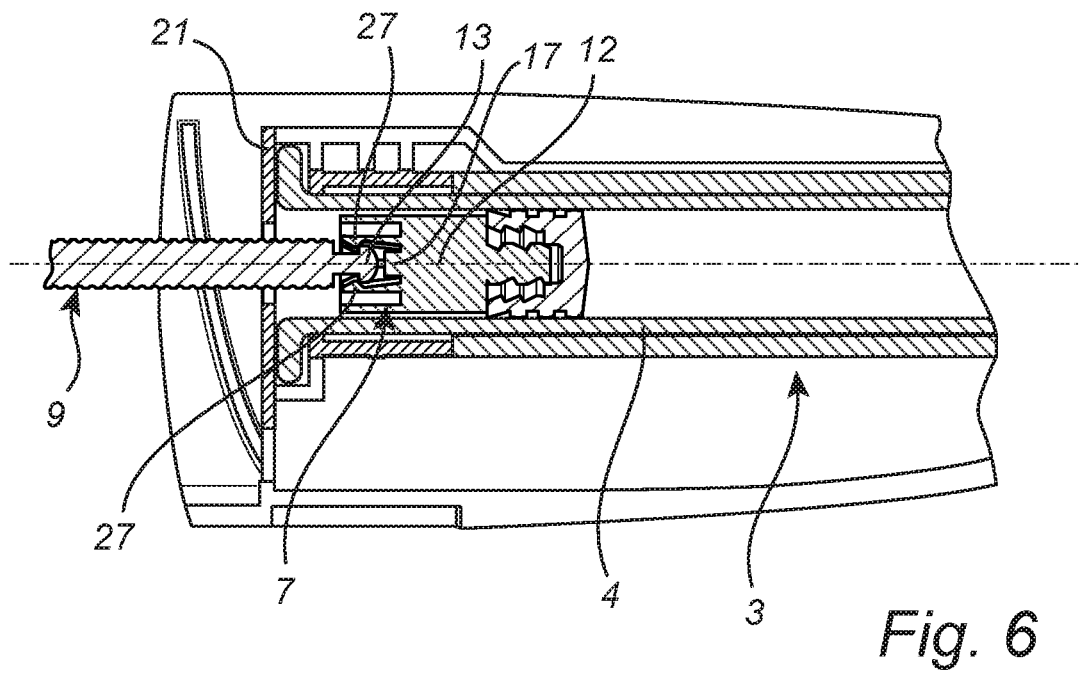
FIG. 6 is still yet another partly sectional views showing a part of the injection device of FIG. 1 in different operational stages.

When the user stops operating the operation button 11, the forward rotational movement of the plunger rod 9 is stopped, and additionally, the injection device 1 is arranged, i.e. its drive unit 8 is programmed, to reverse the plunger rod a small distance, as shown in FIG. 6. This distance is to be just enough to cause a small gap between the end surface 25 of the front end portion 13 and the abutment surface 26 of the rod stop portion 17. Thereby the pressure exerted on the liquid by the plunger 10, and more particularly by the front plunger portion 14, is relieved, and the ejecting of the liquid is fully stopped. If the plunger rod 9 would not be reversed, the pressure would decrease slowly for a short time period during a continued ejection of liquid. Consequently, due to the play between the front end portion 13 and the rod stop portion 17 and the retaining portions 27, respectively, drooling is prevented without the operator having to actively move the plunger 10 rearwards. Consequently, the reversal of the plunger rod 9 should be short enough not to cause a pull back of the plunger 10, which would otherwise cause an undesired aspiration, or intake of air or body liquids in the needle 6.

Figure 7:
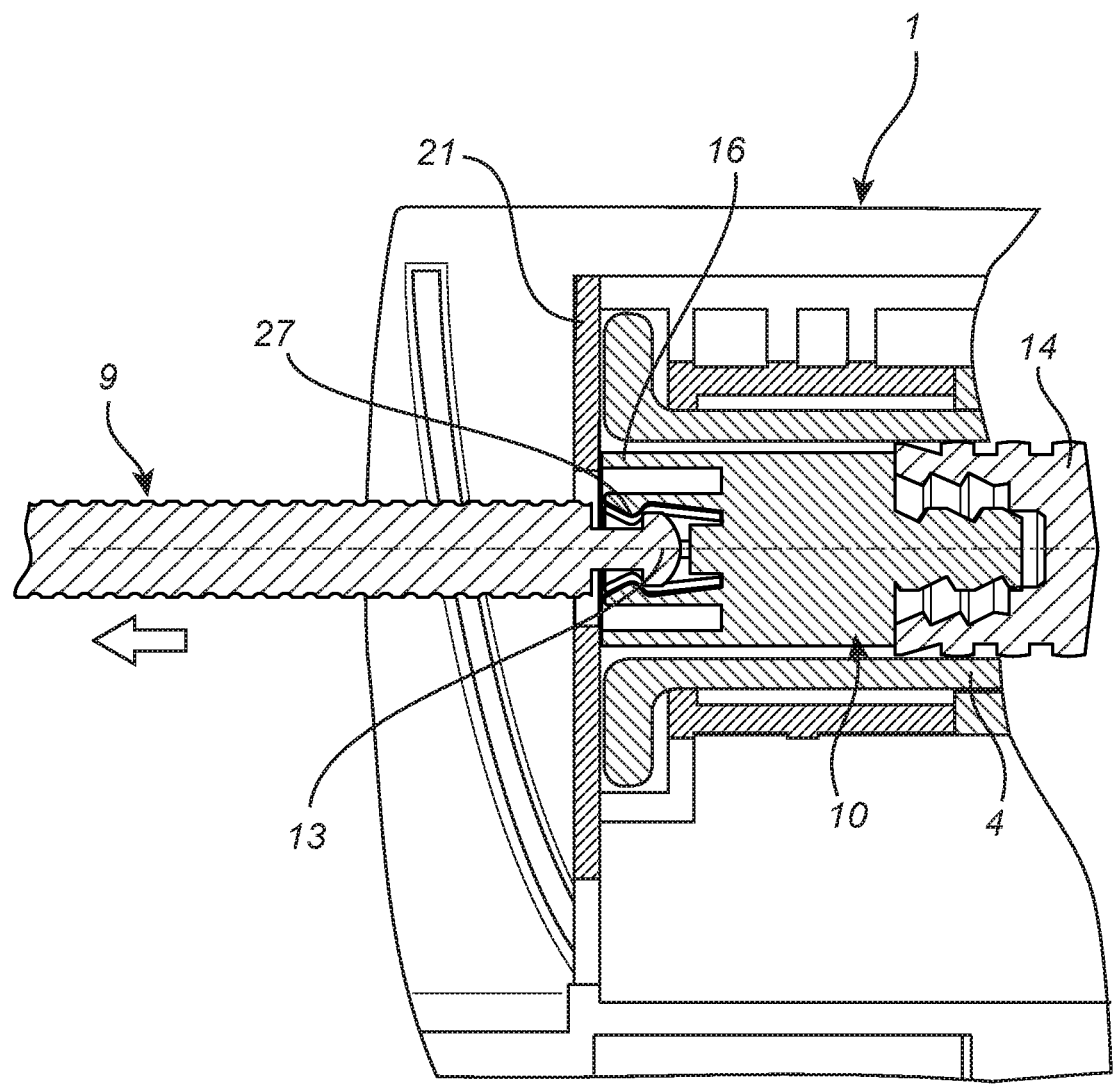
FIG. 7 is another partly sectional views showing a part of the injection device of FIG. 1 in different operational stages.
Figure 8:
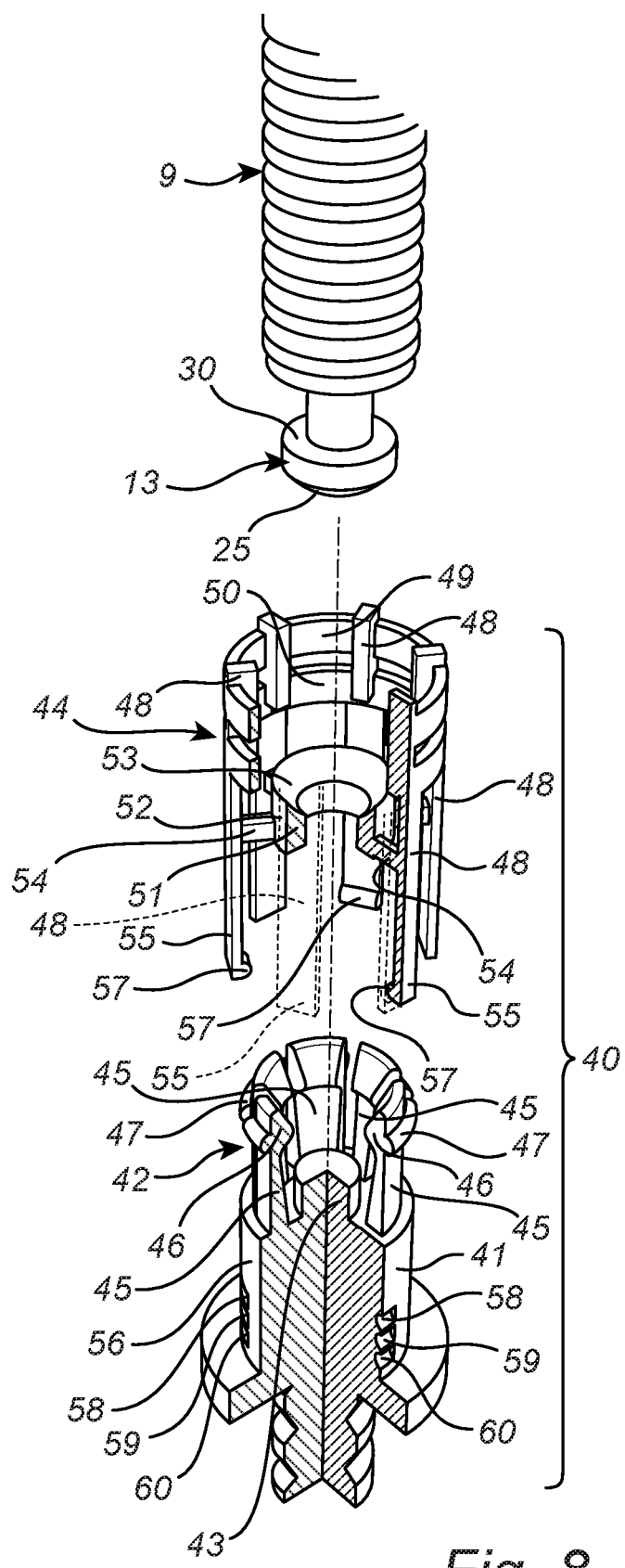
FIG. 8 is an exploded view of a part of a second embodiment of the injection device according to the present invention.
Figure 9:
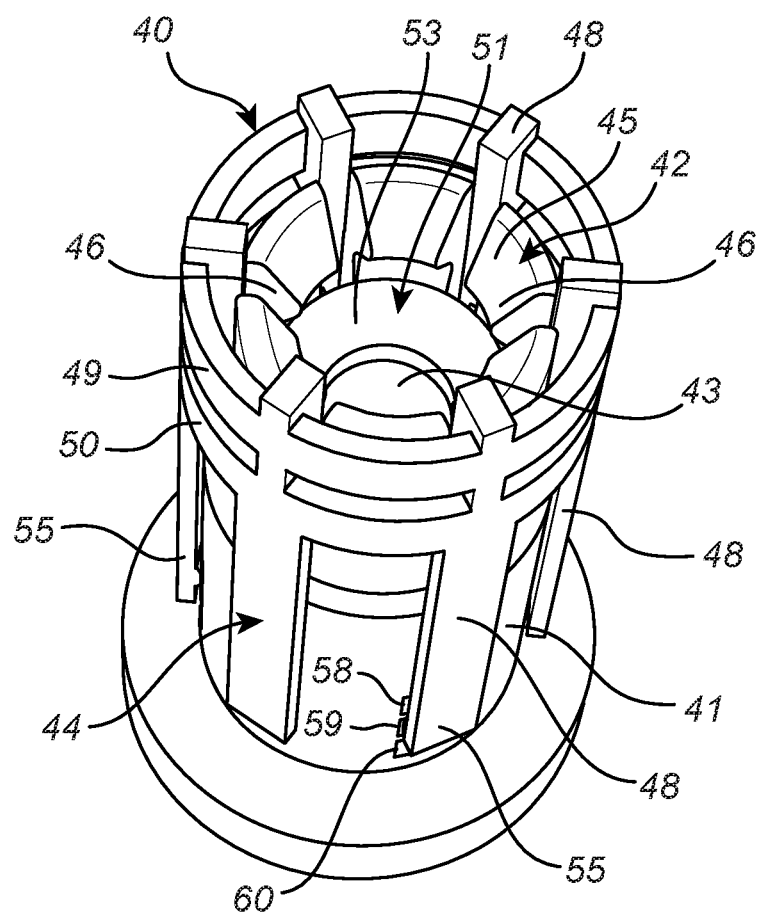
FIG. 9 is a perspective view of the part the second embodiment.
Figures 12A, 12B:
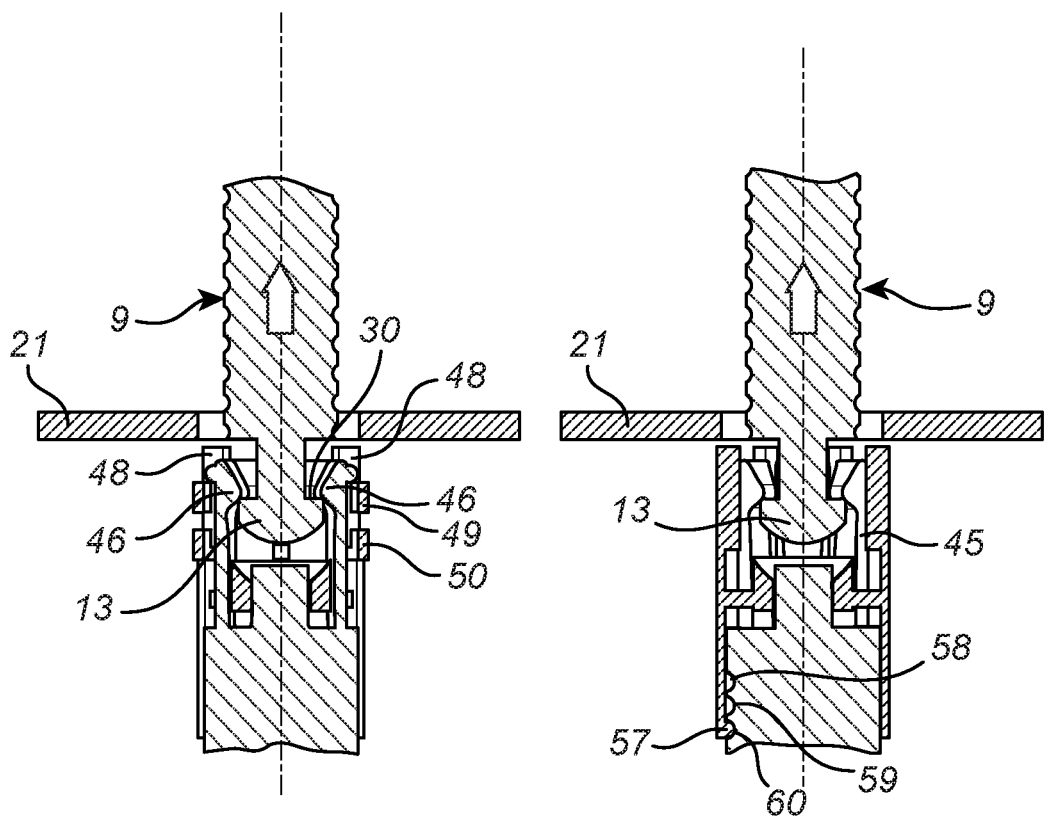
FIG. 12A is another cross-sectional view of the part of the second embodiment.
FIG. 12B is still another cross-sectional view of the part of the second embodiment.

By continued intermittent operation of the operation button 11 for forward movement, several more minor injections can be performed in the same way until the container 4 is emptied, or the injection operation is finished for some other reason. In order to then reverse the plunger 10, the operation button 11 is operated for rearward operation, causing the plunger rod 9 to be retracted, as shown in FIG. 7. The front end portion 13 is provided with a ring shaped rear surface 30 opposite to its front surface 25, and adjacent to the intermediate rod portion 19. When, during the rearward movement, that rear surface 30 engages with the further surfaces 29 of the retaining portions 27, the plunger 10 is pulled rearwards until it reaches the rear end of the container 4, and the cartridge 3. There the rod connector 12 is stopped when the rear end of the outer wall section 15 impinges against the disposable cap 21. When the plunger rod 9 continues rearwards its front end portion 13 forces the tongues 22 to bend outwards when the front end portion 13 passes the retaining portions 27, and thus the entrance opening 18, and leaves the rod connector 9. Finally, the front end portion 13 passes the disposable cap 21, and it is possible to remove the used cartridge 3.

Another operation that is often performed in conjunction with injections is aspiration, i.e. that the plunger 10 of the device 1 is reversed far enough to cause a suction into the needle 6 and container 4. Such aspiration is of course possible to perform with this device 1, by making a part reversal instead of the full reversal just described.

According to a second embodiment of the injection device all parts except for the rod connector are the same as in the first embodiment, and will therefore not be described again. When the same reference numerals as in the first embodiment are used they indicate similar parts. Referring now to FIGS. 8-12B, the rod connector 40 comprises a base portion 41, an inner wall section 42 being integral with, and extending rearwards from, the base portion 41, a rod stop portion 43, which is similar to the rod stop portion 17 of the first embodiment, and an outer wall section 44, which is movable relative to the base portion 41, and thus relative to the inner wall section 42.

The inner wall section 42, like in the first embodiment, comprises several circularly arranged tongues 45, extending rearwards from the base portion 41, with gaps between the tongues 45. Each tongue 45 comprises a retaining portion 46 having the same extension and shape as in the first embodiment. Additionally, each tongue 45 is provided with an outer protrusion 47, which is bump shaped and which is arranged close to a free end, or rear end, of the tongue 45, and on the opposite side of the tongue 45 compared to the retaining portion 46.

The outer wall section 44 is longitudinally movable relative to the inner wall section 42, i.e. in the rearward-forward direction. The outer wall section 44 comprises several longitudinally elongated post elements 48, positioned in the gaps between the tongues 45, a rear ring 49, and a front ring 50, which is longitudinally parallel to the rear ring 49. The rear and front rings 49, 50 are integral with the post elements 48, wherein the rear and front rings 49, 50 extend outside of the tongues 45. There is a gap between the rear and front rings 49, 50. The outer wall section 44 further comprises a rod seat 51 at the centre thereof. The rod seat 51 has a tubular portion 52, which is positioned concentrically of the rod stop portion 43, and a ring shaped collar portion 53 encircling the periphery of the tubular portion 52 at its rear end. The collar portion 53 has a curved surface, which mates with the bulging front surface 25 of the front end portion 13. The post elements 48 are integral with the rod seat 51, and they are connected with the rod seat 51 via a respective spoke element 54. Front end portions 55 of the post elements 48 extend along the outer surface 56 of the base portion 41 of the rod connector 40. The end portions 55 of some of the post elements 48 are provided with a respective inner protrusion 57. At each post element 48 having such an inner protrusion 57 the base portion 41 is provided with three consecutive recesses 58, 59, 60 which are arranged to be able to receive the inner protrusion 57 of the post element 48. Thus, at each post element 48, the recesses 58 are arranged in a row longitudinally of the base portion 41 of the rod connector 40. The inner protrusion 57 of the post element 48 is received in one of the recesses 58, 59, 60. During operation of the injector device 1, in a similar way that has been described in conjunction with the first embodiment of the injector device 1, the movable outer wall section 44 moves between predetermined positions, which are determined by the recesses 58 and the engagement between the recesses 58 and the inner protrusions 57, as follows.

Initially, as shown in FIGS. 10A and 10B, the outer wall section 44 is in a rearmost position, where the inner protrusion 57 of each post element 48 having an inner protrusion is in engagement with the rearmost recess 58. In this position, the outer protrusions 47 of the tongues 45 are located in the gap between the rear and front rings 49, 50. The collar portion 53 of the rod seat 51 is located a distance rear of the end surface of the rod stop portion 43. When the plunger rod 9 is moved forwards into the rod connector 40, and has passed the entrance opening defined by the retaining portions 46 of the tongues 45, the front surface 25 of the front end portion 13 engages with the collar portion 53. During continued forward movement of the plunger rod 9, the second wall portion 44 is brought along forwards until the front end portion 13 reaches the rod stop portion 43. Thus, the tubular portion 52 of the rod seat 51 is moved along the rod stop portion 43, which is pin shaped. Furthermore, the inner protrusion 57 at the front portion 55 of the post element 48 is moved forward to a middle recess 59, with which it engages, while the post element 48 elastically bends outwards during the passage of the area between the rearmost and the middle recesses 58, 59. The position reached thereby is shown in FIGS. 11A and 11B. During the same movement of the outer wall section 44, the rear ring 49 engages with the outer protrusions 47 of the tongues 45 and urges them inwards, such that the tongues 45 bend inwards. Thereby, the retaining portions 46 of the tongues 45 become positioned behind the rear surface 30 of the front end portion 13 and define an opening the diameter of which is smaller than the largest diameter of the front end portion 13. Thereby, when the drive device 8 is reversed to perform an aspiration, the plunger rod 9 abuts on the further surfaces 29 of the retaining portions 46 of the tongues 45 and pulls the rod connector 40 along in the rearward movement.

When the cartridge 3 is to be replaced, and the plunger rod 9 is retracted to leave the cartridge 3, the rear ends of the post elements 48 will eventually impinge on the disposable cap 21 and halt the rod connector 40. Then the front end portion 13 will continue to pull the inner wall section 42 rearwards, which causes the outer protrusions 47 of the tongues 45 to move to a space rear of the rear ring 49, and causes the inner protrusions 57 of the post elements 48 having such an inner protrusion 57 to move from the middle recess 59 to the frontmost recess 60. Since the tongues 45 are now in their idle state, the clamping force of the post elements 48 keeping the retaining portions 46 in the frontmost recesses 60 is enough to retain the inner wall section 42 such that the plunger rod 9 can exit the rod connector 40, and the container 10 to enable replacement of the cartridge 3.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single unit may fulfill the functions of several items recited in the claims. The mere fact that certain measures are recited in mutually different dependent claims does not indicate that a combination of these measured cannot be used to advantage. Any reference signs in the claims should not be construed as limiting the scope.

The invention claimed is:

1. An exchangeable cartridge for an injection device for delivering a liquid composition, the cartridge comprising
a container having a front end and a rear end, and
a plunger slidably arranged within the container, wherein the plunger is connectable with a plunger rod of the injection device, wherein the container is arranged to receive the plunger rod from its rear end,
wherein the plunger comprises
a rod connector connectable with a front end portion of the plunger rod, the rod connector having a base portion, an outer wall section extending rearwards from the base portion, an inner wall section extending rearwards from the base portion, and a rod stop portion encircled by the inner wall section, wherein the inner wall section comprises several tongues protruding rearwards from the base portion and defining an entrance opening for the plunger rod, wherein the inner wall section is arranged to receive a front end portion of the plunger rod through the entrance opening, wherein the tongues are provided with retaining portions, which are arranged to retain the front end portion of the plunger rod during retraction of the plunger rod,
wherein the container is provided with a disposable cap, which covers at least a part of an opening of the container at the rear end of the container, and which constitutes a rear stop for the rod connector,
wherein the outer wall section is longitudinally movable relative to the inner wall section and comprises a plurality of longitudinally elongated posts, wherein end portions of more than one of the longitudinally elongated posts are provided with a respective inner protrusion, and wherein the base portion, at each longitudinally elongated post having such an inner protrusion, is provided with consecutive longitudinally spaced recesses arranged to receive the inner protrusion of the longitudinally elongated post.

2. The exchangeable cartridge according to claim 1, further comprising a sleeve enclosing the container and being configured for mounting of the cartridge at a housing of the injection device.

3. The exchangeable cartridge according to claim 2, wherein the disposable cap is an integral portion of the sleeve.

4. The exchangeable cartridge according to claim 1, wherein a rear end of the outer wall section of the rod connector is arranged to abut the disposable cap in a rearmost position.

5. The exchangeable cartridge according to claim 1, wherein a width of the entrance opening is smaller than a maximum width of the front end portion of the plunger rod, and is larger than or equal to a width of a rod portion adjacent to and rear of the front end portion of the plunger rod, wherein the tongues are resilient for enabling the front end portion of the plunger rod to pass the entrance opening upon exerting an opening force on the tongues.

6. The exchangeable cartridge according to claim 1, wherein each retaining portion comprises a rear surface, which extends radially inwards in a forward direction of the container.

7. The exchangeable cartridge according to claim 1, wherein the rod stop portion comprises a central pin protruding rearwards from the base portion.

8. The exchangeable cartridge according to claim 1, wherein the entrance opening and the rod stop portion are arranged at a distance to each other which enables a longitudinal play between the front end portion of the plunger rod on one hand and the entrance opening and the rod stop portion on the other hand, when the rod connector is connected to the front end portion of the plunger rod, thereby enabling the front end portion of the plunger rod to move back and forth between the entrance opening and the rod stop portion without moving the plunger.

9. The exchangeable cartridge according to claim 1, wherein the plurality of longitudinally elongated posts are positioned in gaps between the tongues.

10. The exchangeable cartridge according to claim 9, wherein the outer wall section comprises a rear ring and a front ring, which is longitudinally parallel to the rear ring, wherein the rear and front rings are integral with the longitudinally elongated posts, wherein the rear and front rings extend outside of the tongues, and wherein there is a gap between the rear and front rings.

11. The exchangeable cartridge according to claim 1, wherein the several consecutive longitudinally spaced recesses are arranged to be able to releasably receive the inner protrusion of the longitudinally elongated posts to removably couple the inner protrusion to a corresponding recess of the several consecutive longitudinally spaced recesses.

12. The exchangeable cartridge according to claim 1, wherein the outer wall section further comprises a rod seat at the center thereof, wherein the rod seat has a tubular portion which is positioned concentric with the rod stop portion, and a ring shaped collar portion encircling the periphery of the tubular portion at its rear end, wherein the collar portion has a curved surface, which mates with a bulging front surface of the front end portion of the plunger rod, and wherein the longitudinally elongated posts are integral with the rod seat, and are connected with the rod seat via a respective spoke element.

13. The exchangeable cartridge according to claim 1, wherein the outer wall section is a tubular portion.

14. An injection device for delivering a liquid composition, comprising a generally elongated housing holding an exchangeable cartridge according to claim 1.

* * * * *